(12) United States Patent
Scheckel (10) Patent No.: US 8,926,492 B2
(45) Date of Patent: Jan. 6, 2015

(54) HOUSING FOR A FUNCTIONAL ELEMENT

(71) Applicant: ECP Entwicklungsgesellschaft mbH, Berlin (DE)

(72) Inventor: Mario Scheckel, Berlin (DE)

(73) Assignee: ECP Entwicklungsgesellschaft mbH, Berlin (DE)

( * ) Notice: Subject to any disclaimer, the term of this patent is extended or adjusted under 35 U.S.C. 154(b) by 0 days.

(21) Appl. No.: 14/265,542

(22) Filed: Apr. 30, 2014

(65) Prior Publication Data

US 2014/0223724 A1    Aug. 14, 2014

Related U.S. Application Data

(62) Division of application No. 13/146,452, filed on Oct. 11, 2011.

(51) Int. Cl.
    *A61M 1/10*    (2006.01)

(52) U.S. Cl.
    CPC .................................. *A61M 1/1025* (2013.01)
    USPC ......................................................... 600/16

(58) Field of Classification Search
    USPC ............................... 623/3.1–3.28; 600/16–18
    See application file for complete search history.

(56) References Cited

U.S. PATENT DOCUMENTS

| | | | |
|---|---|---|---|
| 3,510,229 A | 5/1970 | Smith et al. | |
| 3,568,659 A | 3/1971 | Karnegis | |
| 3,802,551 A | 4/1974 | Somers | |
| 3,812,812 A | 5/1974 | Hurwitz | |
| 4,014,317 A | 3/1977 | Bruno | |
| 4,207,028 A | 6/1980 | Ridder | |
| 4,559,951 A | 12/1985 | Dahl et al. | |
| 4,563,181 A | 1/1986 | Wijayarathna et al. | |
| 4,679,558 A | 7/1987 | Kensey et al. | |
| 4,686,982 A | 8/1987 | Nash | |
| 4,747,821 A | 5/1988 | Kensey et al. | |
| 4,749,376 A | 6/1988 | Kensey et al. | |
| 4,753,221 A | 6/1988 | Kensey et al. | |
| 4,801,243 A | 1/1989 | Norton | |
| 4,817,613 A | 4/1989 | Jaraczewski et al. | |
| 4,919,647 A | 4/1990 | Nash | |
| 4,957,504 A | 9/1990 | Chardack | |
| 4,969,865 A | 11/1990 | Hwang et al. | |
| 4,995,857 A | 2/1991 | Arnold | |
| 5,011,469 A | 4/1991 | Buckberg et al. | |
| 5,040,944 A | 8/1991 | Cook | |
| 5,042,984 A | 8/1991 | Kensey et al. | |
| 5,052,404 A | 10/1991 | Hodgson | |
| 5,061,256 A | 10/1991 | Wampler | |
| 5,092,844 A | 3/1992 | Schwartz et al. | |

(Continued)

FOREIGN PATENT DOCUMENTS

| CA | 1008330 A1 | 4/1977 |
|---|---|---|
| CA | 2311977 A1 | 12/2000 |

(Continued)

*Primary Examiner* — Amanda Patton
(74) *Attorney, Agent, or Firm* — Marshall & Melhorn, LLC (57) ABSTRACT

A method for selectively expanding and compressing a housing for a blood pump is described. The housing is provided in a compressed state. The housing has a slack, flexible membrane with a plurality of groups of compressed formed parts with gaps between the individual formed parts. The formed parts are moved together outwardly against the membrane to expand the membrane. A fully expanded membrane and housing is formed where the formed parts completely abut against the membrane in a gap free relationship with respect to one another.

7 Claims, 4 Drawing Sheets

(56) References Cited

U.S. PATENT DOCUMENTS

| | | |
|---|---|---|
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nusser et al. |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,927,068 B2 | 4/2011 | Mcbride et al. |
| 7,934,909 B2 | 5/2011 | Nuesser et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0195004 A1 | 8/2006 | Jarvik |
| 2008/0132747 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 1/2014 | Schulz et al. |

FOREIGN PATENT DOCUMENTS

| | | |
|---|---|---|
| CA | 2701809 A1 | 4/2009 |
| CA | 2701810 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19711935 A1 | 4/1998 |
| DE | 69407869 T2 | 4/1998 |
| DE | 29804046 U1 | 6/1998 |
| DE | 69017784 T3 | 4/2000 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0480102 A1 | 4/1992 |
| EP | 0560000 A2 | 9/1993 |
| EP | 0629412 B1 | 1/1998 |
| EP | 0884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |

(56) References Cited

FOREIGN PATENT DOCUMENTS

| | | |
|---|---|---|
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 9401148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 | 10/2000 |
| WO | 0107760 A1 | 2/2001 |
| WO | 0107787 A1 | 2/2001 |
| WO | 2001083016 A2 | 11/2001 |
| WO | 2003057013 A2 | 7/2003 |
| WO | 03103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

HOUSING FOR A FUNCTIONAL ELEMENT

This application is a divisional application claiming priority to U.S. patent application Ser. No. 13/146,452 filed on Oct. 11, 2011.

The invention resides in the field of mechanical engineering and precision engineering and can be used advantageously in particular in the medical field.

In particular in the field of medicine, high demands are placed upon housings for functional elements which are used for example in invasive or micro-invasive operations. Such housings must often be very small just as the corresponding functional elements in order as far as possible not to cause damage during introduction into the body of a patient or to require small incisions. Micro-invasive operations are thus possible in order to assist for example bodily functions, such as blood circulation, i.e. the pumping capacity of the heart, or similar.

In particular for micropumps which can be operated in the body of the patient, pump housings which can be introduced into the body with the respective pump via a blood vessel are known. For this purpose, often both the pump blades of the pump and the pump housing are deformable between a compressed state for movement through a body vessel and an expanded state in which the pump is operated according to plan.

Various approaches to this are known from the literature, as to how components of this type can be compressed or expanded in the body in a controlled manner. It is known for example to use so-called shape memory materials which can be brought into various shapes for example by temperature changes. However, it should be noted in conjunction with the use of shape memory materials that these often have non-linear mechanical properties which are partially difficult to control and in addition are cost-intensive.

A solution is known from the patent document DE 10 2004 054 714 A1, in which both the impeller of a micropump and the housing thereof is expanded by a relative axial displacement of the pump drive shaft relative to a catheter. As a result, the housing is folded between the compressed and the expanded state.

From WO 00/2003103745 A2, a system in which the pump housing likewise is radially expanded by an axial relative movement of two components relative to each other is known.

DE 10 2004 054714 A1 teaches a blood pump with a flexible housing in the form of a hose that is supported by elastic sticks directed parallel to a rotor axis and extending each from the proximal end of the housing nearly to its distal end.

US 2008/0132748 shows a blood pump with a rotor that is moving in a rib cage housing formed by bendable ribs. The length of the ribs is comparable to the length of the housing. The ribs exhibit an arcuate shape and in the extended state of the housing it has an ellipsoidal or prolate-spheroid form.

WO 94/05347 describes a blood pump with a rotor that is placed in a housing that is provided with a lattice of bars in order to shield the rotor. The bars have the form of one-piece filaments extending in the longitudinal axis of the rotor. This filament cage can be expanded by displacement of the ends of the filaments.

Against the background of the state of the art, the object underlying the invention is to produce a housing which can be compressed or expanded with as simple means as possible, the constructional complexity requiring to be minimised. Nevertheless, the housing should have the stability required for operation.

The object is achieved according to the invention by the features of patent claim 1.

The invention relates to a housing for a functional element, in particular for use in the medical field in naturally occurring vessels in the body, the housing wall of which has a slack, flexible, tensionable membrane with a plurality of formed parts secured thereon which support the membrane in the tensioned state thereof by forming one or more groups of formed parts wherein the parts of each group support one another in the tensioned state of the membrane.

The separately formed parts allow for folding and compressing of the housing in all directions without substantial resistance forces.

For this purpose, the parts of a group may be in touching contact to other parts of the same group, when the membrane is in its tensioned state. The parts may abut against each other, engage one in the other or overlap each other. In the non-tensioned state of the membrane, they may or may not touch other parts of the same group.

All the components are advantageously configured for this purpose from biocompatible materials. The formed parts may be individually attached to the housing as separate bodies.

Advantageously, at least one group of formed parts forms a rib-like linear structure in the tensioned state of the membrane. The one or more rib-like structures may have straight or circular or semicircular form or arc form. These rib-like or arc-like structures may be directed parallel to a longitudinal axis of the housing.

The parts of at least one group may as well build a two-dimensional shield form that covers a part of the surface of the housing.

The corresponding formed parts are advantageously stable in shape and rigid and can be configured as injection moulded parts, in particular made of plastic material, and are essentially bar- or plate-shaped.

Furthermore, the invention can advantageously be configured in that at least one of the formed parts has a support surface which abuts against the membrane in the tensioned state.

Also a plurality of formed parts in the tensioned state can abut against the membrane flatly in an adjacent manner, in particular on the inside thereof, in order to form a covering of the membrane which supports the latter and does not impede a fluid flow within the housing.

The formed parts can advantageously be connected exclusively to the membrane, i.e. have no connection to a further component in the interior of the housing. The positioning of the housing with respect to a functional element, in particular a pump, can then be achieved by support arms which are described further on.

The formed parts can be connected rigidly by their entire support surface which abuts against the membrane or be connected also only to a part of the support surface, in particular to a delimiting edge of the support surface.

The connection of the formed parts to the membrane can be produced for example as an adhesive joint.

In the tensioned state of the membrane, the formed parts abutting against the inside of the housing/of the membrane can essentially cover the membrane and also abut against each other.

The membrane is consequently reinforced and protected effectively from damage from the inside.

The formed parts can partially overlap each other and as it were lie one above the other in the manner of scales or in the manner of shingles. Hence a particularly good support and gap-free covering of the membrane is ensured.

The formed parts can also partially engage one in the other in order to be mutually supported and positioned.

Hence the formed parts in the tensioned state of the housing can form an inherently stable support body which supports the membrane from inside.

The invention relates in addition also to a device having a housing according to the above-described type and having a functional element, the device having a fluid pump which produces an excess pressure in the housing which leads to tensioning of the membrane.

Hence the moveability of the slack, flexible membrane and the moveability of the formed parts in the non-tensioned state of the membrane is used for the purpose of tensioning the membrane by means of an excess pressure in the housing without a notable counter-force and for stabilising and supporting said membrane by means of the abutting formed parts in the tensioned state. If necessary, when starting up the pump if this is disposed in the housing, it must be accepted that the pump blades of the pump rub on parts of the housing until the housing is expanded according to plan by the excess pressure building up and a pump gap is configured between blade tip and housing.

If the pump is switched off again, then the housing collapses and can be retracted together with the functional element through the naturally occurring vessel in the body or an artificial vessel—e.g. a lock.

In contrast to other concepts for compressible and expandable housings, the compression movement of the housing, after stopping the pump, encounters no noteworthy elastic counter-force which would make the compression process difficult. The described behaviour when retracting into an artificial vessel and during transport through this vessel turns out to be particularly advantageous since little force need be expended hereby for the translatory movement through the vessel.

The expansion or compression of the housing, if a functional element different from a pump is disposed in the latter, can also be achieved in that the housing is subjected to pressure with an externally disposed fluid pump or the pressure is reduced for collapsing.

A typical application for the invention is the production with a blood pump so that, during operation, the pump conveys blood and hence builds up an internal pressure which expands the housing for example in a ventricle as desired.

If a fluid pump is located in the housing, then advantageously a suction opening and a catheter connection are provided. The suction opening can have for example a suction cage which, on the one hand, retains coagulated blood components away from the pump and, on the other hand, protects the naturally occurring bodily tissue outside the housing from injury by the pump blades if a rotor pump is used.

If the housing is used for a blood pump that works without a rotor and instead has a pulsatile pumping element, for example in the form of a cushion with variable volume, then the formed parts may support the membrane of the housing and at the same time, the parts are not endangered by the movement of a rotor while the housing is extending. Therefore, the housing may advantageously be used as housing of a pump with a drive element that comprises a cushion with variable volume. Usually, this pump concept requires appropriate valves in the openings of the housing that are controllable by a control unit.

Support arms advantageously serve to position and centre the housing relative to a functional element located in the latter, in particular a pump rotor. These can extend for example radially from the housing up to the functional element or possibly up to a drive shaft or a component mounted on the latter and be supported there on at least one formed part and/or be secured on the membrane.

In the case where the radially inner end of the support arms is fixed in the axial direction, an axial movement of the housing results in the course of the compression/expansion movement at the same time if the support arms are not flexible or not provided with at least one bending joint.

The support arms can advantageously engage in the expanded state of the housing, the corresponding locking devices being intended to be configured such that bending of the support arms is effected as soon as the excess pressure in the pump housing falls below a specific threshold value.

Hence the support arms in the expanded state of the housing exert an additional support effect.

Even if each support arm is provided with a plurality of joints, these can engage in a stable manner at a corresponding angle which corresponds to the desired state in the expanded state of the housing until the housing collapses due to the lowering of the excess pressure. Then the support arms can bend to compress the housing.

The support arms can also form a suction cage at the same time in the inlet region of the housing in which a fluid is suctioned in.

Apart from a housing of the described type or a device with such a housing, the invention relates in addition also to a method for the production of a housing in which formed parts are secured firstly on a flat membrane and thereafter the membrane is rolled up and fitted together to form a hose.

In this way, the formed parts can be secured easily on the membrane in an automated method, for example by glueing, without spatial problems impeding this process. The housing is thereafter produced from the flat membrane as a hose which can advantageously taper conically at one of its ends to form a catheter connection. At the opposite end of the hose, support arms can be provided in order to form a suction cage.

In the following, the invention is shown in a drawing with reference to an embodiment and subsequently explained.

There are thereby shown

FIG. 1 basically the construction of a catheter with a heart pump introduced through a blood vessel into a ventricle, FIG. 2 in a side view, the housing in the compressed state (above) and in the expanded state (below), FIG. 3 a side view of another housing in the compressed state (above) and in the expanded state (below), FIG. 4 the housing in the compressed state in a cross-section, FIG. 5 the housing in a partially expanded state in a cross-section, FIG. 6 the housing in the expanded state in cross-section, FIG. 7 the housing in partially expanded state with an incorporated pump, FIG. 8 the housing in the expanded state with an expanded pump in a cross-section, FIG. 9 a three-dimensional view of the membrane in the flat state with formed parts glued on, and also FIG. 10 the formed parts on the membrane in the expanded state with a representation of the mutually engaging ends of the formed parts.

Figure 1:
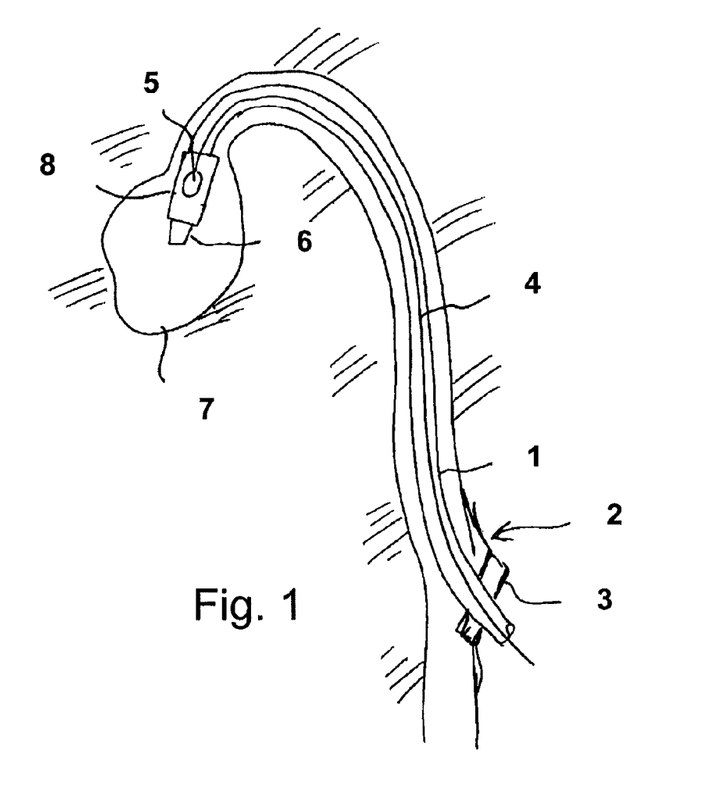

In a longitudinal section, FIG. 1 shows schematically a catheter 1 which is introduced into a blood vessel 2 of a human body by means of a lock 3 and is conveyed through this vessel into the ventricle 7.

A functional element 5 with a housing 8 is located at the end of the catheter 1, the functional element 5 comprising a blood pump with an impeller and the housing 8 having a suction cage 6 on its end.

A shaft 4 which extends up to the pump 5 and actuates the impeller there with the pump blades is provided within the catheter 1.

The housing 8 is shown in an at least partially expanded state which it assumes after introduction into the ventricle and the pump being set in operation.

The housing and the pump are described subsequently in more detail with reference to the remaining Figures.

Figure 2:
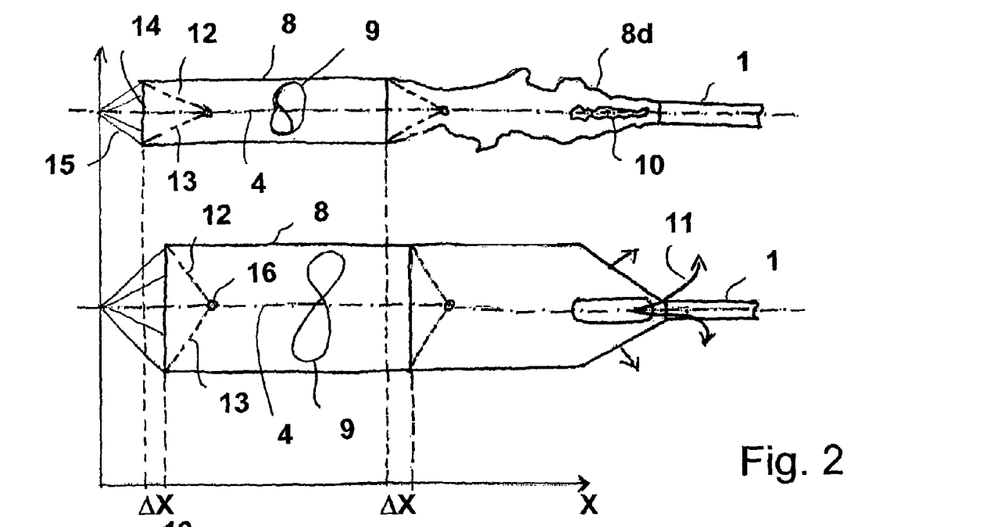

In FIG. 2, a side view of the housing 8 is represented at the top in the compressed state, said housing being connected to the catheter 1 and receiving a pump impeller 9 in the likewise compressed state in its interior. The pump impeller can have for example a hub and pump blades folded onto the latter.

The housing 8 has a conically tapered part 8d which is connected to the catheter 1 and which has, in the region in front of the catheter, at least one opening 10 via which the liquid can flow out. This is represented by the arrows 11 for a plurality of openings. Hence the transport of the fluid from a location of lower pressure—in the ventricle—to a location in which the pressure is increased locally by the energy input of the pump—can be produced above the aortic sinus (sinus aortae). The aortic valve (valva aortae) situated in front of the opening 10 acts as valve and prevents the fluid from flowing back into the ventricle 7.

The housing 8 is constructed essentially cylindrically at least in the expanded state (at the bottom) and comprises, in its outer region, a membrane which is fitted on its inside with formed parts. The formed parts are dealt with further on in more detail.

FIG. 2 shows in addition support arms 12, 13 which, on the one hand, are secured on at least one point on the housing 8 and, on the other hand, on the shaft 4 which extends along the dot-dash line which in addition also represents the cylindrical axis of symmetry of the arrangement.

The support arms 12, 13 are folded in in the compressed state in the longitudinal direction of the shaft 4 and are located at an acute angle to the latter.

If the pump impeller 9 is set in operation so that the pump begins to rotate, then a flow is produced in that liquid from the surroundings of the housing 8 is suctioned into the opening 14 through a suction cage 15 and is accelerated towards the catheter 1. In the pump housing 8, an excess pressure relative to the surroundings which expands the pump housing 8 radially is hence produced. To the same degree as the pump housing 8 expands radially, the pump blades of the pump can be deployed and consequently the power of the pump can be increased.

In the lower part of FIG. 2, the housing 8 is represented in the fully expanded state, the pump impeller 9 also being fully opened out. In this state, the pump provides its full power and the support arms 12, 13 are spread relative to the shaft 4 at an obtuse angle.

In this state, the supports arms 12, 13 can engage for example at their articulation point 16 at a rigid angle so that they support the expanded state of the housing 8.

In the course of the expansion of the pump housing 8, also an axial movement/compression of the housing 8 by the amount $\Delta X$ takes place due to the spreading of the support arms 12, 13, as is indicated in FIG. 2.

Figure 3:
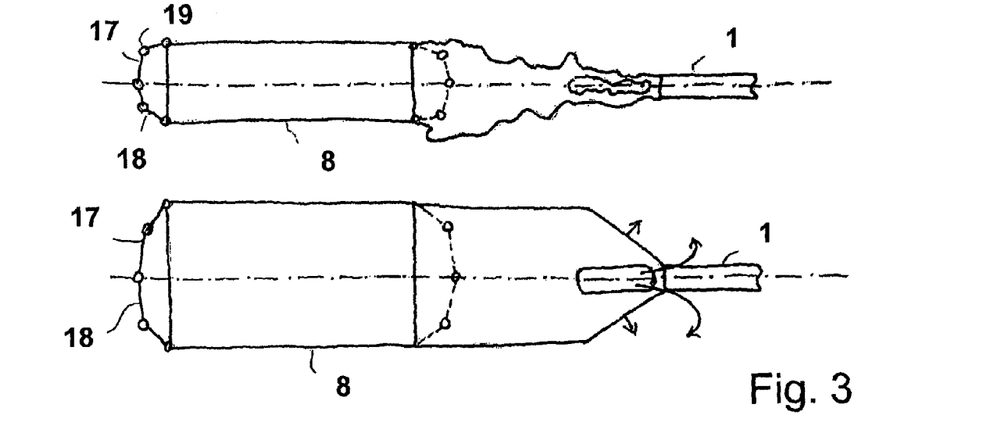

A similar pump housing 8 as in FIG. 2 is shown in FIG. 3, the support arms 17, 18 differing from those shown in FIG. 2 in that each support arm has per se one or more joints 19.

These joints 19 effect a more flexible adaptation of the support arms 17, 18 to the degree of expansion of the housing 8 and lead to the axial compression/displacement of the housing 8 during the tensioning being reduced or eliminated.

Also the articulated support arms 17, 18 can engage in a specific position so that, even in this constellation, an additional supporting of the expanded housing is possible. The engaged position can be overcome during collapse of the housing 8 by applying a specific threshold force.

In addition, the constellation of FIG. 3 has the particular feature that the support arms 17, 18 curve outwards from the housing 8 towards the housing exterior so that the support arms can form at the same time a convenient suction cage 15.

Figure 4:
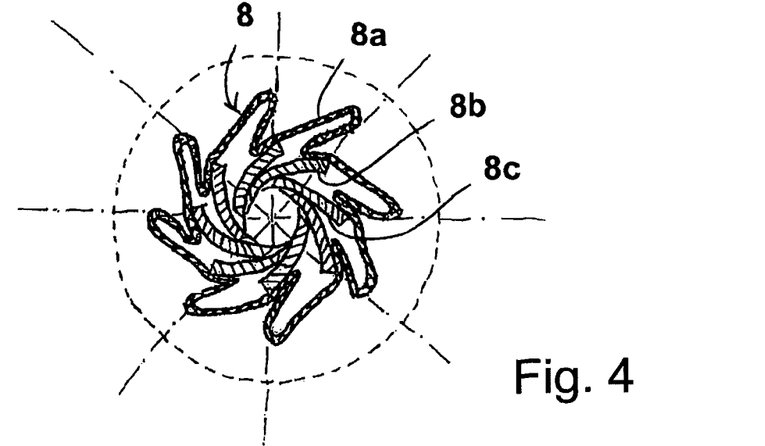

FIG. 4 shows, in a cross-sectional view, the housing 8 in the compressed state, it being clear in this representation that the housing 8 has a membrane 8a and formed parts 8b, 8c which are present folded together in the compressed state of the housing. The individual formed parts 8b, 8c are connected respectively merely in a partial region of their support surface 22 to the membrane 8a by glueing. The pump rotor is not illustrated in the representation of FIGS. 4, 5 and 6 for the sake of clarity.

Figure 5:
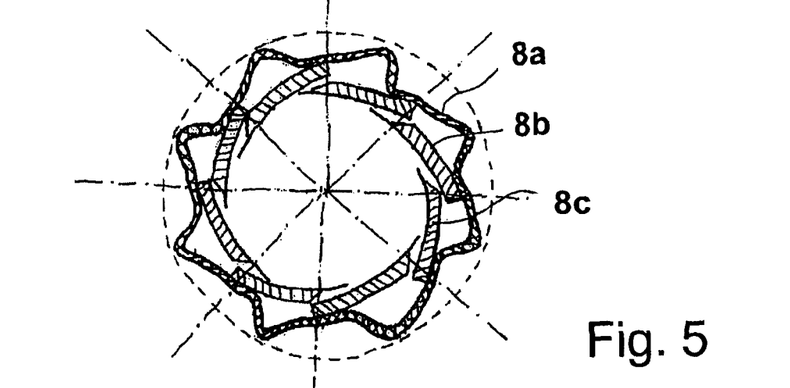

FIG. 5 shows the housing in a partially expanded state, the formed parts 8b, 8c approaching the membrane 8a with their support surfaces.

Figure 6:
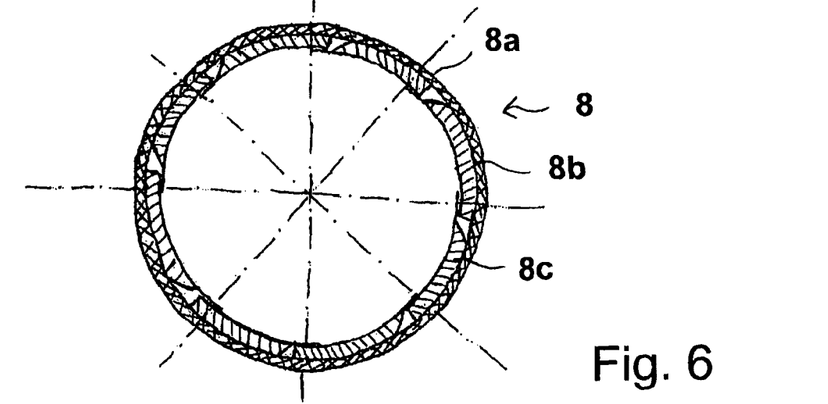

In FIG. 6, the housing 8 is shown in the completely expanded state, the formed parts 8b, 8c abutting completely against the membrane 8a and hence also not impeding a flow within the housing. In this state, the formed parts 8b, 8c mutually touch and overlap so that they mutually engage and mutually support their position. Hence, they form a scale-like reinforcement of the membrane and contribute substantially to the stability of the housing.

Figure 7:
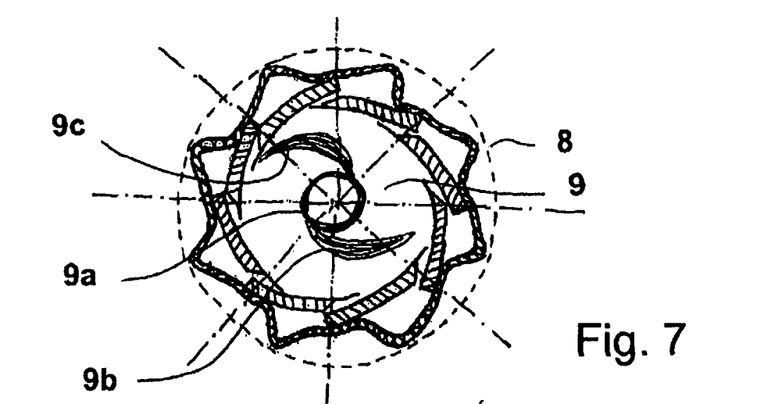

In FIG. 7, the pump housing 8 with a pump rotor 9 is represented in cross-section, the pump rotor 8 having a hub 9a and pump blades 9b, 9c. The pump blades 9b, 9c are folded against the hub 9a at least partially, which is made possible in that the pump blades are secured either in an articulated manner on the hub or are configured per se to be elastically flexible.

Figure 8:
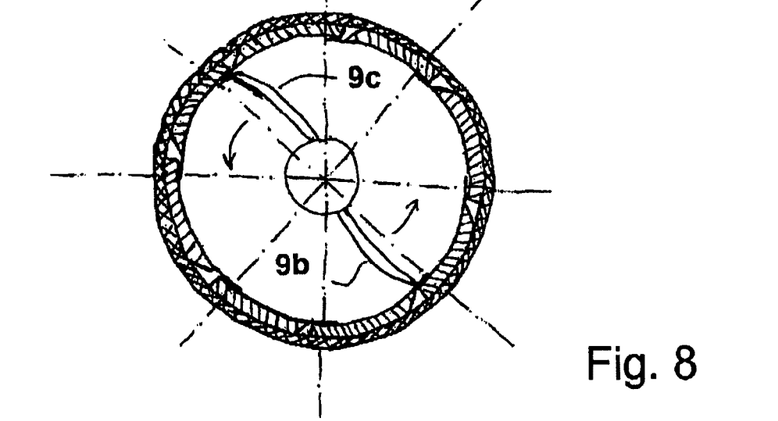

In the representation of FIG. 8, the housing 8 is completely expanded and the pump blades 9b, 9c are deployed to the maximum so that the maximum pump power is achieved in this constellation.

Figure 9:
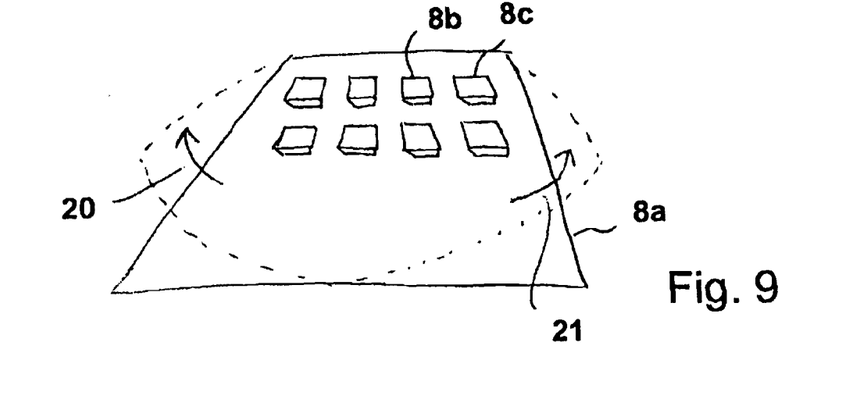

In FIG. 9, finally a flat membrane 8a is shown, on which formed parts 8b, 8c are secured by glueing before the membrane 8a, as indicated by the arrows 20, 2, is rolled up and fitted together to form a hose.

Figure 10:
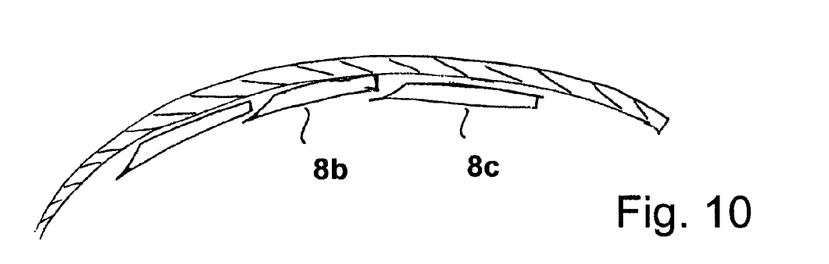

FIG. 10 shows, enlarged, the mutual engagement of formed parts 8b, 8c which have an asymmetrical configuration and are situated one above the other in a shingle- or scale-like manner.

As a result of this type of production, a housing according to the invention can be produced particularly easily and economically. The membrane can thereby be produced as a slack, flexible foil, elastically or non-elastically, and the formed parts 8b, 8c can be produced typically as plastic material injection moulded parts. The shingle- or scale-like positioning in the region of the formed parts 8b, 8c situated one above the other makes possible an advantageous compensation for the process-induced deviations in length and position of the formed parts. Greater production tolerances can be accepted and hence production costs can be lowered. An at least partially automated production is made possible.

The housing according to the invention hence makes possible simple expandability with low costs and low constructional complexity without external force expenditure, simply by producing a fluid pressure in the housing. This can be produced particularly easily when used with a pump. Even during compression of the housing, practically no counterforces are produced so that the housing possible with a catheter and possibly with a lock can be removed again easily from the body of a patient.

The invention claimed is:

1. A method for selectively expanding and compressing a housing for a blood pump, comprising:
    providing a housing in a compressed state and having a slack, flexible membrane with a plurality of groups of compressed formed parts therein with gaps between said individual formed parts;
    moving said formed parts together outwardly against said membrane to expand said membrane; and
    forming a fully expanded membrane and housing wherein the formed parts completely abut against the membrane in a gap free relationship with respect to one another.

2. The method of claim 1, wherein said fully expanded housing forms a fluid passage wherein said formed parts do not impede fluid flow within said passage.

3. The method of claim 1, wherein in said compressed state, said formed parts at least partially overlap one another.

4. The method of claim 1, wherein in said fully expanded state said formed parts engage one another to support said membrane.

5. The method of claim 1, wherein said formed parts are secured to said membrane.

6. The method of claim 1, wherein a fluid pump selectively creates an excess pressure in the housing which expands said formed parts into said housing.

7. A method for selectively expanding and compressing a housing for a blood pump, comprising:
    providing a housing in a compressed state and having a slack, flexible membrane with a plurality of groups of compressed formed parts therein with gaps between said individual formed parts;
    moving said formed parts together outwardly against said membrane to expand said membrane;
    forming a fully expanded membrane and housing wherein the formed parts completely abut against the membrane in a gap free relationship with respect to one another; and
    producing an excess pressure in said housing with a fluid pump which leads to tensioning of the membrane.

* * * * *